United States Patent [19]
Riordan

[11] Patent Number: 5,334,509
[45] Date of Patent: Aug. 2, 1994

[54] METHOD FOR DETECTING INTESTINAL PATHOGEN DIENTAMOEBA FRAGILIS

[76] Inventor: Neil H. Riordan, 7715 E. 32nd North, Wichita, Kans. 67226

[21] Appl. No.: 964,874

[22] Filed: Oct. 22, 1992

[51] Int. Cl.$^5$ .................... C12Q 1/04; G01N 33/48
[52] U.S. Cl. .................... 435/34; 435/29; 436/63; 436/164; 436/800; 424/3; 424/7.1
[58] Field of Search ............ 436/63, 164, 800; 435/29, 34, 38, 947; 424/2, 3, 7.1

[56] References Cited

U.S. PATENT DOCUMENTS

| | | | |
|---|---|---|---|
| 4,190,328 | 2/1980 | Levine et al. | 436/800 X |
| 4,268,434 | 5/1981 | Higerd et al. | 435/882 X |
| 4,751,188 | 6/1988 | Valet | 436/63 |
| 4,783,401 | 11/1988 | Horan et al. | 435/34 |
| 4,906,561 | 3/1990 | Thornthwaite | 436/63 X |
| 5,075,556 | 12/1991 | Fan et al. | 436/63 X |

OTHER PUBLICATIONS

Grendon et al., Public Health Reports, vol. v106, Issue n3, May–Jun. 1991, p. 322(4).
Kodak Laboratory & Research Products, catalog No. 53, 1987, p. 255.
Biology of Microorganisms –5th edition, 1988, p. 604.
Diagnostic Parasitology, Clinical Laboratory Manual, 2nd edition, 1979, pp. 99–101 and 105.
Medical Parasitology, A Self-Instructional Text, 1979, pp. 158–159.
Clinical Diagnosis & Management by Laboratory Methods–16th edition, 1979, pp. 1759–1765 and 1769.

Primary Examiner—James C. Housel
Assistant Examiner—Maureen M. Wallenhorst
Attorney, Agent, or Firm—John W. Carpenter

[57] ABSTRACT

A method and apparatus for producing detectable intestinal parasites. The method includes obtaining an intestinal mucosa sample (e.g. feces) having intestinal parasites, such as *Dienamoeba fragilis*; and contacting the obtained intestinal mucosa sample with an acridine base compound (e.g. acridine orange and/or acridine yellow, etc.) such that the intestinal parasites become differentially stained and detectable by a human eye when viewed through a fluorescence microscope. The apparatus includes a kit or the like which includes at least one vessel or vial. Preferably, two vials are contained within the kit with one vial having an isotonic salt solution including a salt, such as sodium chloride, potassium phosphate, etc., and the other vial containing an acridine biological staining compound.

20 Claims, 7 Drawing Sheets

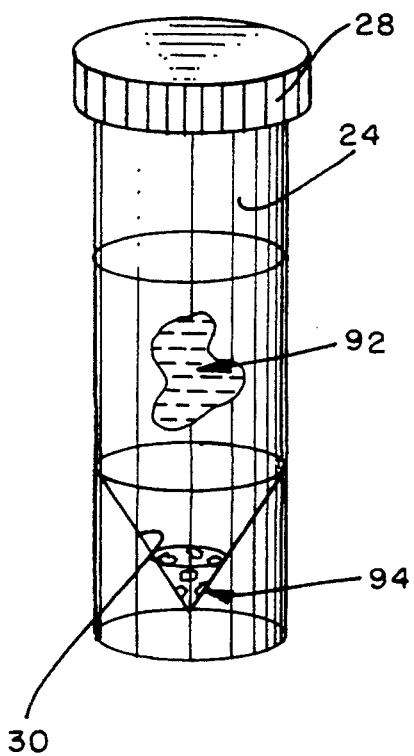
FIG. 11
FIG. 12
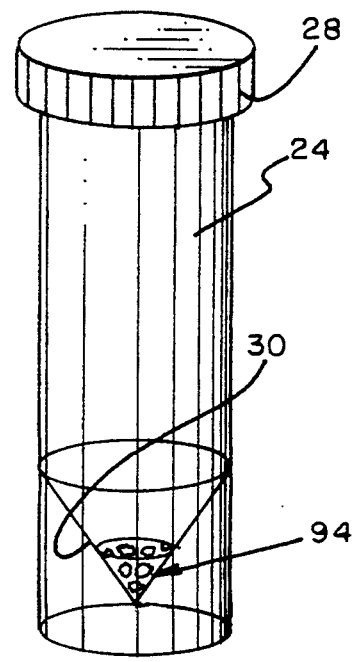

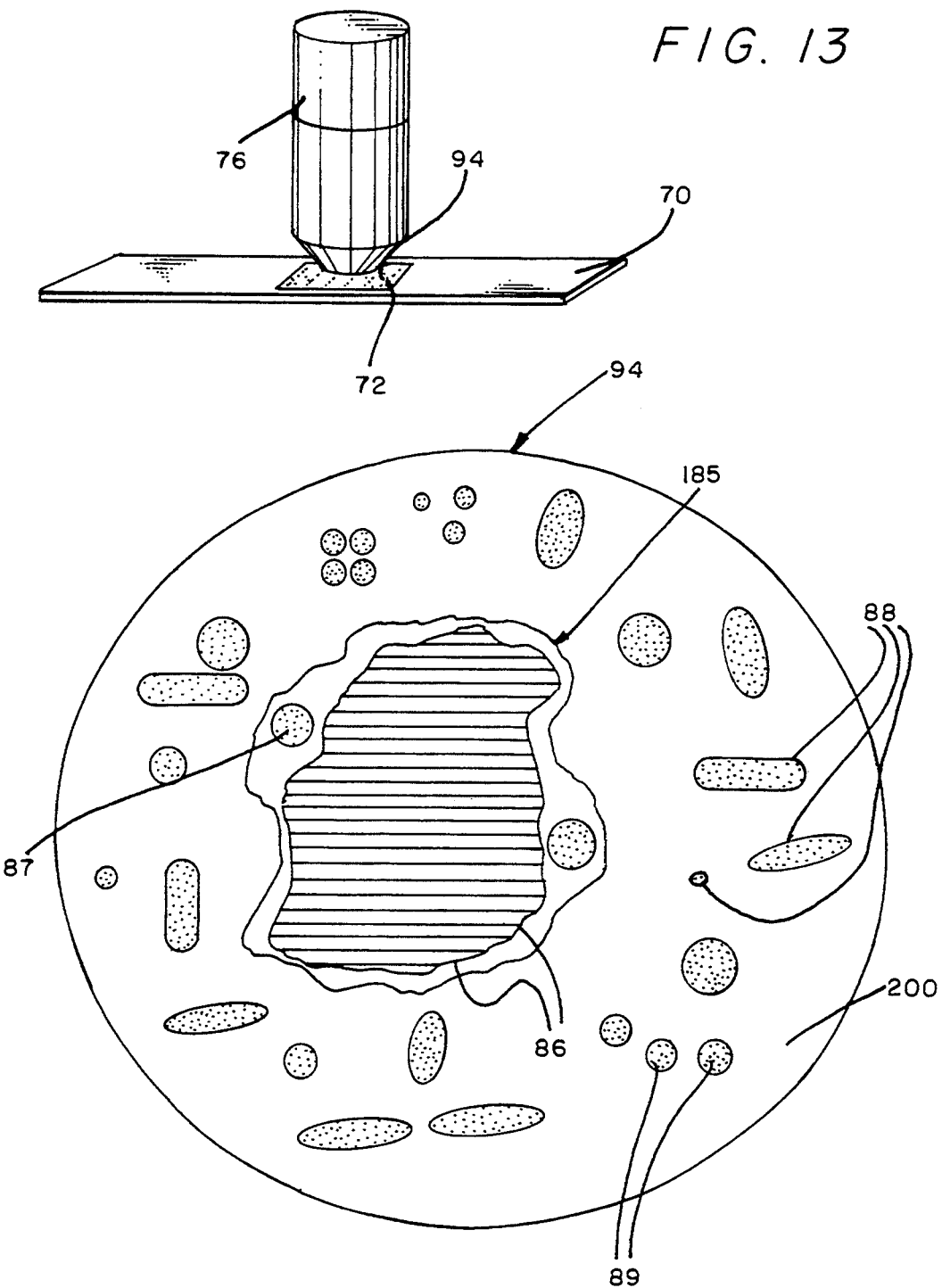
FIG. 13
FIG. 14
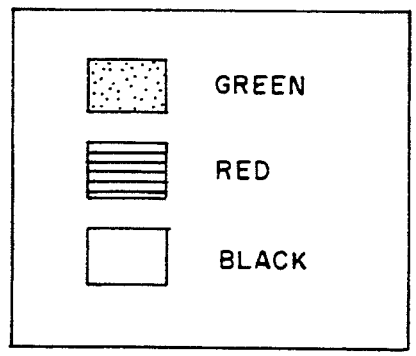

METHOD FOR DETECTING INTESTINAL PATHOGEN DIENTAMOEBA FRAGILIS

BACKGROUND OF THE INVENTION

1. Field of the Invention

This invention is related to detecting intestinal parasites. More particularly, this invention provides a method and apparatus for detecting intestinal parasites in feces, especially the protozoa *Dientamoebo fragilis* is in feces, particularly human feces; and samples obtained from the mucosa of the intestinal tract, especially the human intestinal tract.

2. Description of the Prior Art

A conventional method for the detection of intestinal parasites consists of obtaining a fecal sample or intestinal mucosa sample and examining it macroscopically and microscopically for the presence of parasites. In the case of protozoan parasites,. microscopic examination is necessary for identification of trophozoite and cyst stages. Some intestinal protozoa can be identified microscopically in fresh, unfixed samples, but traditionally, samples are fixed with a fixative, such as formaldehyde, polyvinyl alcohol, sodium acetate-acetic acid-formalin, or Schaudinn's fixative. Samples may or may not be subjected to concentration techniques such as sedimentation and floatation methods. The sample, whether concentrated or not or fixed or not, can be examined at this stage for protozoa. The sample is commonly subsequently stained using the trichrome staining method after fixation of a small amount of sample to a microscope slide.

*Dientamoebo fragilis* is a pathogenic protozoan parasite of the large intestine and cecum of human beings that has no cyst stage. Infection with this protozoa has been associated with diarrhea, abdominal pains, pruritus and loose stools. It has been suggested that *Dientamoeba fragilis* causes acute and chronic colitis through an invasive ulcerative process. Because of the lack of a cyst stage, present laboratory procedures for detection of *Dientamoeba fragilis* in fecal samples are unreliable. A recent study has indicated that *Dientamoeba fragilis* in an infected fecal sample can go undetected.

Therefore, what is needed and what has been invented is a reliable method for detecting intestinal parasites, especially *Dientamoeba fragilis*.

SUMMARY OF THE INVENTION

The present invention accomplishes its desired objects by broadly providing a method for producing detectable intestinal parasites comprising obtaining feces or an intestinal mucosa sample having intestinal parasites; and contacting the obtained feces or intestinal mucosa sample with an acridine base compound, whereupon the intestinal parasites become differentially stained and detectable when viewed by a human eye, especially with the employment of a fluorescent microscope. The acridine base compound is preferably in a solution such as an aqueous solution. The aqueous solution is preferably an isotonic aqueous solution containing a compound selected from the group consisting of sodium chloride, potassium chloride, potassium phosphate, sodium phosphate, glucose, and mixtures thereof. Alternatively, the isotonic aqueous solution may be any salt solution, such as commercially available Hank's Balanced Salt Solution (HBSS) or Phosphate Buffered Saline (PBS). The isotonic aqueous solution may also contain a pH indicator, such as phenol red. More preferably, the isotonic aqueous solution has a pH of from about 5.0 to about 8.0 and optionally further comprises a fixative, such as formalin. The isotonic aqueous solution may optionally further comprise a preservative such as an alcohol (e.g. methanol and/or ethanol, etc.). The intestinal parasite detected is preferably the intestinal pathogenic protozoan *Dientamoeba fragilis*.

The present invention further accomplishes its desired objects by also broadly providing an apparatus for producing detectable intestinal parasites. The apparatus comprises a kit or the like which preferably includes at least one vessel or vial, more preferably a pair of vessels or vials. One of the vessels or vials contains a solution ranging from a hypotonic water to a hypertonic salt solution, preferably an isotonic solution exhibiting an osmolality ranging from about 200 milli Osm/liter to about 400 milli Osm/liter and containing one or more of the following ingredients: NaCl (sodium chloride), KCl (potassium chloride), $KH_2PO_4$ (potassium phosphate), $Na_2HPO_4$ (sodium phosphate), and $C_6H_{12}O_6$ (glucose). The solution may also contain a pH indicator, such as phenol red, and/or a fixative, such as formalin, and/or a preservative, such as an alcohol (e.g. methanol and/or ethanol, etc.). The other vessel or vial contains an acridine compound, preferably in a solution. More preferably, the other vessel or vial contains an acridine staining compound (e.g. acridine orange and/or acridine yellow) in an aqueous solution such as, by way of example only, a salt solution containing one or more of the following ingredients: NaCl (sodium chloride), KCl (potassium chloride), $KH_2PO_4$ (potassium phosphate), $Na_2HPO_4$ (sodium phosphate) and $C_6H_{12}O_6$ (glucose). As previously indicated, the aqueous solution may be any salt solution, such as HBSS and/or PBS.

The fluorescent dye (fluorochrome), acridine orange (AO), is a small, fluorescent, planar cationic vital dye which, in the unfixed cell, complexes with intranuclear nucleic acids as well as other intracellular polyanionic biopolymers. Because of its special affinity for the nucleic acids, AO has the property of differentiating ribonucleic acid (RNA) from deoxyribonucleic acid (DNA). In a solution of optimum acidity, the AO-RNA combination fluoresces an orange-pink color and the AO-DNA combination fluoresces a yellowish-green color. The intensity of fluorescence in each combination depends on the concentrations of respective nucleic acids. When a high concentration of RNA is present such as is the case with fast growing cells, the cytoplasm and the nucleoli may show a fluorescence of a brighter orange-red.

In a laboratory, it was found that the whole of the RNA-containing cytoplasm of the intestinal protozoa *Dientamoeba fragilis* fluoresces a bright orange to red color and that the DNA-containing nucleus or nuclei of the amoeba fluoresce(s) yellow to green in a feces or intestinal mucosa sample that has been exposed to the AO dye. This occurs while most of the remaining objects in the sample, such as bacteria, undigested food, mycobacteria, and epithelial cells fluoresce predominantly green, providing for easily visible differentiation and subsequent ready identification of *Dientamoeba fragilis* in a sample of fecal or intestinal mucosal origin. This bright orange to red fluorescence of *Dientamoeba fragilis* is thought to occur as a function of the high content of RNA in the cytoplasm of the protozoa that is rapidly dividing in the cecum and colon which are located at the end of the intestinal tract.

It is therefore an object of the present invention to provide a method for producing detectable intestinal parasites, especially the intestinal pathogenic protozoan *Dientmoeba fragilis*.

It is another object of the present invention to provide an apparatus for producing detectable intestinal parasites, especially the pathogenic protozoan *Dientamoeba fragilis*.

These, together with the various ancillary objects and features which will become apparent to those skilled in the art as the following description proceeds, are attained by this novel method and apparatus for producing detectable intestinal parasites, a preferred embodiment being shown with reference to the accompanying drawings, by way of example only, wherein:

BRIEF DESCRIPTION OF THE DRAWINGS

FIG. 11 is a perspective view of the vial of FIG. 10 after intestinal mucosa was removed from the cotton-tip of the rod member and suspended in the aqueous solution containing the acridine compound, and after the vial was centrifuged to produce a supernatant and a bottom sediment having differentially stained intestinal parasites;

FIG. 12 is a perspective view of the vial in FIG. 11 after the supernatant has been removed, leaving the bottom sediment having differentially stained intestinal parasites;

FIG. 13 is a perspective view of the differentially stained bottom sediment that was removed from the vial in FIG. 12 and placed on a slide and covered by a coverslip for viewing detectable intestinal parasites (e.g. *Dientamoeba fragilis*) by a fluorescence microscope; and FIG. 14 is a top plan view of the differentially stained bottom sediment mixture as viewed through the fluorescence microscope of FIG. 13 at a high magnification, for viewing intestinal parasites, (e.g. *Dientamoeba fragilis*), typically having an orange to red cytoplasmic color; nuclei, bacteria and undigested food material typically having a green color; and a residual field or background, typically having a black color.

DETAILED DESCRIPTION OF THE INVENTION

Figure 1:
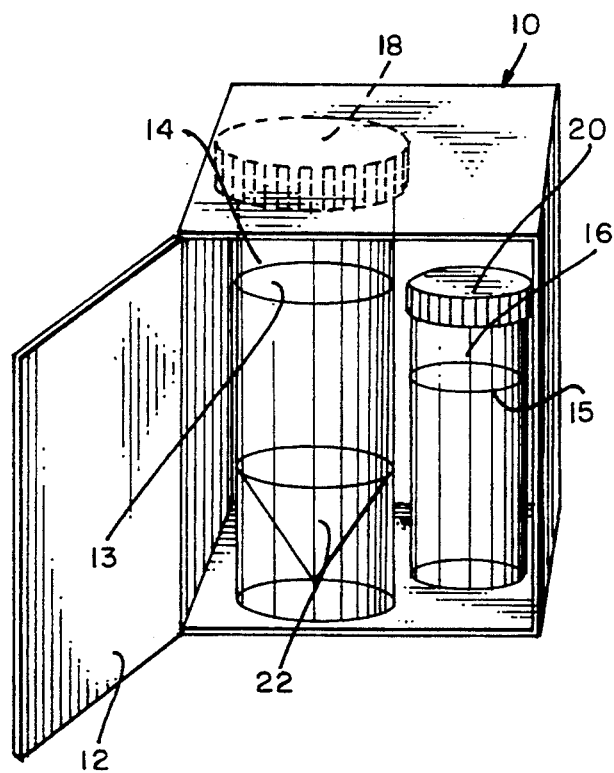
FIG. 1 is a perspective view of a container or kit having two vials, with one vial containing an aqueous solution ranging from a hypotonic water to a hypertonic salt solution (preferably an isotonic solution), and optionally, a fixative and/or a preservative, and with the other vial containing an acridine compound such as the biological staining agent, acridine orange.
Figure 9:
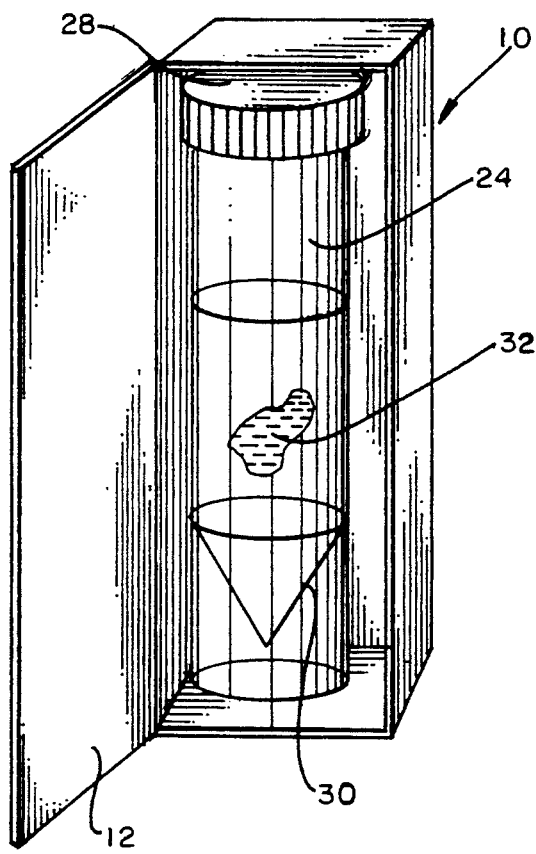
FIG. 9 is a perspective view of another embodiment of the container or kit having one vial containing an aqueous solution ranging from a hypotonic water to a hypertonic salt solution (preferably an isotonic solution and with or without a pH indicator such as phenol red), and an acridine compound (such as acridine orange) and optionally, a fixative and/or preservative.

Referring in detail now to the drawings wherein similar parts of the invention are identified by like reference numerals, there is seen a container or kit, generally illustrated as 10 in FIGS. 1 and 9. The container or kit 10 may be any suitable container or kit 10 manufactured from any material, including pliable material such as pliable plastic, nylon, cloth or the like. The container or kit 10 conveniently includes a pivotally secured side or door 12 which also may be formed from any suitable material including pliable material. The container or kit 10 of this invention may be formed or manufactured into any geometric shape, and thus, the box-like appearing structure in FIGS. 1 and 9 is not intended to limit the scope of the invention.

In the embodiment of the invention and of the container 10 in FIG. 1, the container 10 comprises a pair of vessels or vials 14 and 16 having removable tops 18 and 20, respectively. Each of the vessels 14 and 16 may possess any suitable volume, preferably from about 0.5 ml to about 50.0 ml, vessel 14 more preferably from about 5.0 ml to about 25.0 ml, and vessel 16 more preferably from about 1.0 ml to about 10 ml. Vessel 14 is preferably formed with a funnel or cone-shaped bottom 22, and contains or includes an aqueous solution 13 ranging from hypotonic water to a hypertonic salt solution. Preferably, the aqueous solution 13 in vessel 14 is an isotonic solution exhibiting an osmolality from about 200 milliOsm/liter to about 400 milliOsm/liter, more preferably from about 250 milliOsm/liter to about 350 milliOsm/liter, most preferably about 300 milliOsm/liter, and containing one or more of the following ingredients: NaCl (Sodium Chloride), KCl (Potassium Chloride), $KH_2PO_4$ (Potassium Phosphate), $Na_2HPO_4$ (Sodium Phosphate), and $C_6H_{12}O_6$ (Glucose). The aqueous solution 13 in vessel 14 may optionally include a pH indicator, such as phenol red. The vessel 16 preferably contains a solution or mixture 15 comprising the aqueous solution 13 of or from the vessel 14 (as immediately described in the foregoing sentences) and a biological staining agent comprising an acridine base compound having the general formula: $C_{13}H_9N$ (tricyclic) with an average molecular weight of about 179.2. Acridine typically has the properties of being small colorless needles that are soluble in alcohol, ether or carbon disulfide, and sparingly soluble in hot water. Acridine has the further properties of subliming at about 100° C., a melting point of about 111° C. and a boiling point of about 360° C. As is well known to the artisans skilled in the art, acridine is produced by or derived by extraction with dilute sulfuric acid from the anthracene fraction from coal tar and adding potassium dichromate. The acridine chromate precipitated is recrystallized, treated with ammonia and recrystallized. Preferably, the acridine base compound is selected from the group consisting of acridine hydrochloride [$C_{13}H_9N$ HCl (tricyclic) with an average molecular weight of about 215.7]; acridine -9- carboxylic acid [$C_{14}H_9NO_2$ (tricyclic) with an average molecular weight of about 223.2]; acridine mustard; acridine mutagens; acridine yellow [$C_{15}H_{15}N_3.HCl$ (tricyclic) having an average molecular weight of about 273.8]; acridine orange base [$C_{17}H_{19}N_3$ (tricyclic) having an average molecular weight of about 265.4]; and acridine orange [3,6-bis [Dimethylamino] acridine]; and mixtures thereof. More preferably, the acridine base compound is selected from the group consisting of acridine orange, acridine orange base, acridine yellow, and mixtures thereof. Most preferably the acridine base compound is acridine orange, more particularly acridine hemi (zinc chloride) salt [$C_{17}H_{20}ClN_3 \cdot \frac{1}{2} ZnCl_2$ (tricyclic) having an average molecular weight of about 370]. The concentration of the acridine base compound (especially the acridine orange) in the solution 15 or mixture 15 ranges from about 0.04 micrograms/milliliter to about 5 milligrams/milliliter, more preferably from about 0.4 micrograms/milliliter to about 100 micrograms/milliliter, and most preferably from about 5 micrograms/milliliter to about 40 micrograms/milliliter.

In another preferred embodiment of the present invention and of the container 10 in FIG. 1, vessel 14, in addition to containing the aqueous solution 13 as more specifically described above and optionally a pH indicator, the aqueous solution 13 in vessel 14 comprises from about 1% by volume to about 70% by volume, more preferably from about 5% by volume to about 15% by volume, of a fixative, such as formalin (i.e. sodium acetateacetic acid-formalin) and/or polyvinyl alcohol, and/or Schaudinn's fixative and/or a preservative such as an alcohol, e.g., methanol and/or ethanol, etc. If a fixative is used in conjunction with a preservative, the quantity of each is to be in any suitable percentage by volume, such as, by way of example only, the fixative and preservative mixture may comprise from about 1% to 99% by volume of the final solution.

In the preferred embodiment of the present invention and of the container 10 in FIG. 9, the container 10 contains a vessel or vial 24 having a removable top 28 and a funnel or cone-shaped bottom 30. The vessel or vial 24 may be identical to the vessel 14 and possess any suitable volume, such as from about 0.5 ml to about 50.0 ml., more preferably from about 5.0 to about 25.0 ml. The vessel or vial 24 contains or includes an aqueous solution 32 ranging from hypotonic water to a hypertonic salt solution. Preferably, the aqueous solution 32 in vessel or vial 24 is an isotonic solution exhibiting an osmolality from about 200 milliOsm/liter to about 400 milliOsm/liter, more preferably from about 250 milliOsm/liter to about 350 milliOsm/liter, most preferably about 300 milliOsm/liter, and containing one or more of the following ingredients: NaCl (Sodium Chloride), KCl (Potassium Chloride), $KH_2PO_4$ (Potassium Phosphate), $Na_2HPO_4$(Sodium Phosphate), or $C_6H_{12}O_6$ (Glucose). The aqueous solution 32 in vessel 24 also comprises the biological staining agent comprising the acridine base compound as generally and more specifically described above. More particularly and as previously indicated, the preferred and more preferred and most preferred species of the acridine base compound are the same as previously described above. The concentration of the acridine base compound (especially the acridine orange) in the aqueous solution 32 in vessel 24 preferably ranges from about 0.04 micrograms/milliliter to about 5 milligrams/milliliter, more preferably from about 0.4 micrograms/milliliter to about 100 micrograms/milliliter, and most preferably from about 5 micrograms/milliliter to about 40 micrograms/milliliter.

In another preferred embodiment of the present invention and of the container 10 in FIG. 9, vessel 24, in addition to containing the aqueous solution 32 as more specifically described above and optionally a pH indicator, the aqueous solution 32 in vessel 24 comprises from about 1% by volume to about 70% by volume, more preferably from about 5% by volume to about 15% by volume, of a fixative, such as formalin (i.e. sodium acetateacetic acid-formalin) and/or polyvinyl alcohol, and/or Schaudinn's fixative and/or a preservative such as an alcohol, e.g., methanol and/or ethanol, etc. If a fixative is used in conjunction with a preservative, the quantity of each is to be in any suitable percentage by volume, such as, by way of example only, the fixative and preservative mixture may comprise from about 1% to 99% by volume of the final solution.

In order to obtain an intestinal mucosa sample if feces is not available, a rectal swab technique is employed. The rectal swab technique optionally consists of the insertion of a lubricated anuscope (not shown in the drawings) into the anal canal of a patient, and the insertion of, and subsequent swabbing of the mucosa with one or more sterile swabs, generally illustrated as 40. More specifically, each swab 40 includes a stick 42 having a cotton tip 44 at one of the distal ends (see FIGS. 2 and 10). The cotton tip 44 absorbs and/or gathers intestinal mucosa and feces when swabbed against and/or within the anal canal of a patient. If the intestinal mucosa is to be analyzed for intestinal parasites, especially for *Dientamoeba fragilis*, the rectal swab technique is the more preferred procedure for obtaining an intestinal mucosa sample rather than by the reception of feces from a patient.

Figure 2:
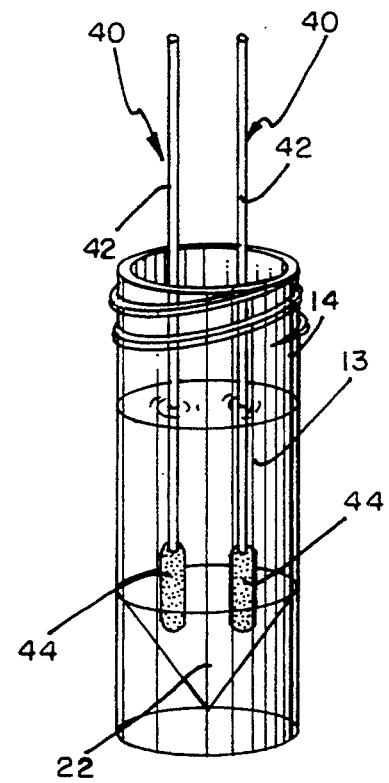
FIG. 2 is a perspective view of the aqueous solution-containing vial (without any biological staining agent) from the container or kit of FIG. 1, having at least one cotton-tip rod member immersed therein after the cotton-tip of the rod member obtained an intestinal mucosa sample from swabbing the rectal area or mucosa of a large intestine of a human being.
Figure 3:
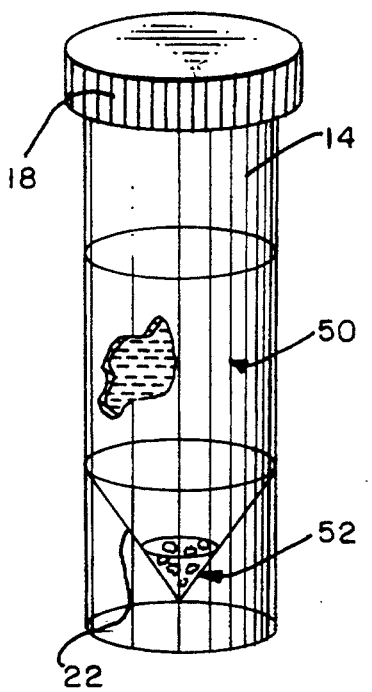
FIG. 3 is a perspective view of the vial of FIG. 2 after intestinal mucosa was removed from the cotton-tip of the rod member and suspended in the aqueous solution, and after the vial was centrifuged to produce a supernatant and a bottom sediment having intestinal parasites.
Figure 4:
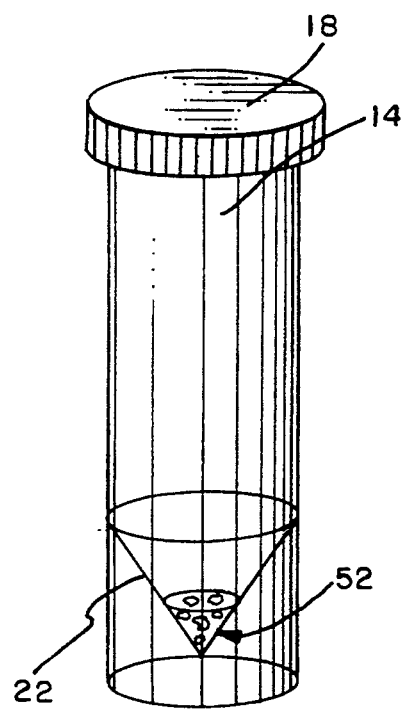
FIG. 4 is a perspective view of the vial in FIG. 3 after the supernatant has been removed, leaving the bottom sediment having intestinal parasites.

After the cotton tip 44 of a sterile swab 40 has obtained an intestinal mucosa sample and for the embodiment of the invention depicted in FIGS. 1–8, the cotton tip 44 is inserted into the previously described aqueous solution 13 (e.g. Hank's balanced salt solution (HBSS)) within the vial 14 and swirled such that the intestinal mucosa sample may pass into the aqueous solution 13 (see FIG. 2). If feces is available, a quantity (e.g. 0.1 to 1.0 cubic centimeters) of the feces is emulsified in the aqueous solution 13. Subsequently, the vial 14 is centrifuged to produce supernatant 50 and sediment 52 (see FIG. 3). The supernatant 50 is slowly decanted or otherwise removed from the sediment 52, leaving the sediment 52 in the bottom of the vial 14, as best shown in FIG. 4.

Figure 5:
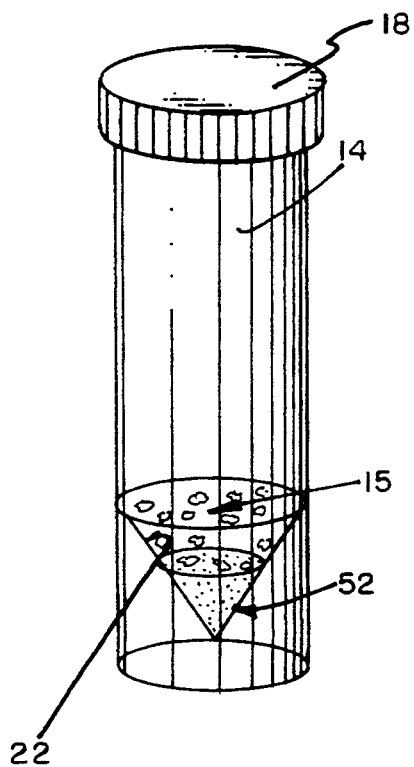
FIG. 5 is a perspective view of the vial in FIG. 4 after a desired volume of the acridine compound has been added to the vial in FIG. 4 from the other, acridine compound-containing vial in FIG. 1.
Figure 6:
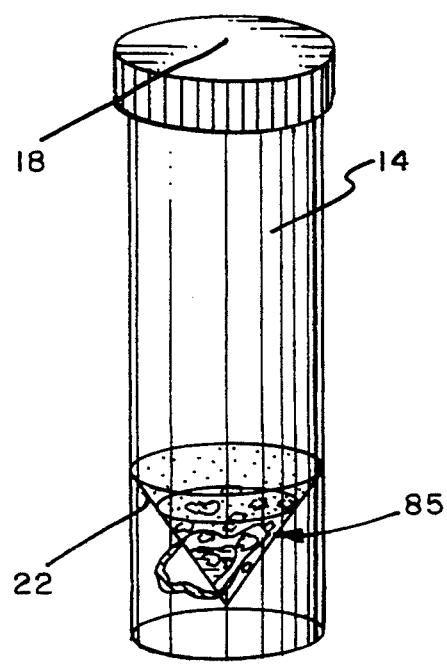
FIG. 6 is a perspective view of the vial in FIG. 5 after the desired volume of the acridine compound has been mixed with the bottom sediment having intestinal parasites, to produce a sediment mixture containing differentially stained intestinal parasites.
Figure 7:
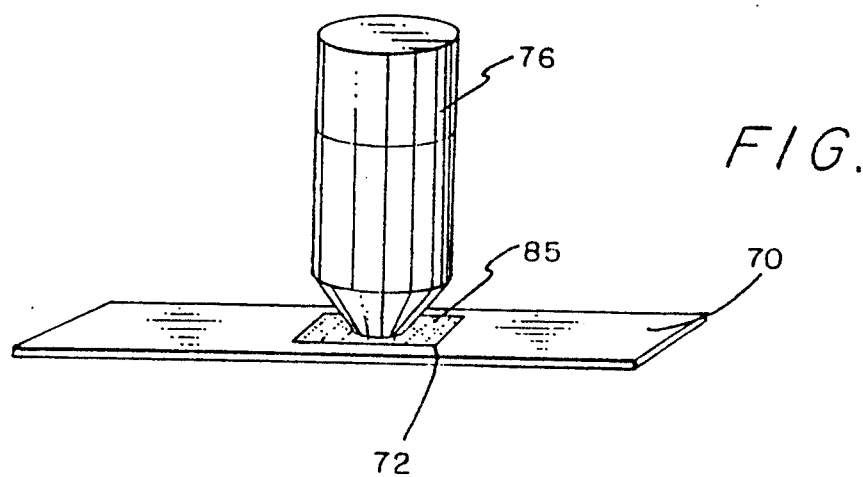
FIG. 7 is a perspective view of the differentially stained bottom sediment that was removed from the vial in FIG. 6 and placed on a slide and covered by a coverslip for viewing detectable intestinal parasites (e.g. *Dientamoeba fragilis*) by a fluorescence microscope.

The solution or mixture 15 (i.e. the aqueous solution 13 plus the biological staining agent (an acridine base compound)) from vessel 16 is added to sediment 52 in vial 14, as best shown in FIG. 5. More specifically the mixture 15 is added to the sediment 52 in a weight or volume ratio varying from about 1:10 to about 10:1, preferably in about a 1:1 volume ratio. After such addition, the solution or mixture 15 is mixed with the sediment 52 to produce an admixture 85 as best shown in FIG. 6. A convenient quantity of the admixture 85 (e.g. one drop or approximately 50 ul) is placed on a microscope slide 70 (see FIG. 7) and a coverslip 72 is superimposed on slide 70 to sandwich the quantity 85. The quantity of admixture 85 is subsequently examined for parasites using a microscope 76 equipped with an ultraviolet light source (e.g. a fluorescence microscope). When the quantity of the admixture 85 is viewed through the fluorescence microscope, the following by way of example only and not by limitation may be seen; intestinal parasites 185 (e.g. *Dientamoeba fragilis*), typically having an orange to red cytoplasmic color 86 and including nuclei with a green color 87; bacteria 88 and undigested food material 89 also both typically having a green color; and a residual field or background 200, typically having a black color.

Figure 10:
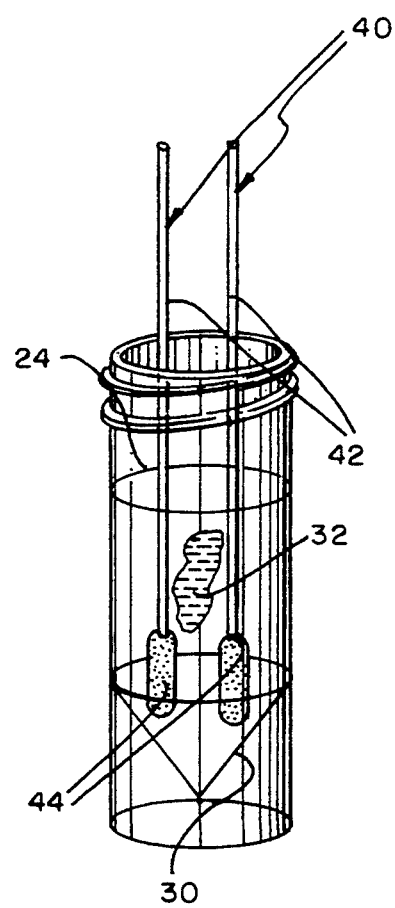
FIG. 10 is a perspective view of the vial in FIG. 9 containing the aqueous solution and the acridine compound, having at least one cotton-tip rod member immersed therein after the cotton-tip of the rod member obtained an intestinal mucosa sample from swabbing the rectal area or mucosa of a large intestine of a human being.

For the embodiment of the invention depicted in FIGS. 9-14, after the cotton tip 44 of a sterile swab 40 has obtained an intestinal mucosal sample, the cotton tip 44 is inserted into the previously described aqueous solution 32 (e.g. HBSS and one of the previously described acridine based compounds) within vial 24 and swirled such that the intestinal mucosa sample may pass into and be suspended in the aqueous solution 32 (see FIG. 10). If feces is available, it is emulsified and from about 0.1 to about 1.0 cubic centimeters of the emulsified feces is suspended in the aqueous solutions 32. Subsequently, the vial 24 is centrifuged to produce supernatant 92, stained sediment 94 (see FIG. 11). The supernatant 92 is slowly decanted or otherwise removed from and/or off the stained sediment 94, leaving the stained sediment, as best shown in FIG. 12. A convenient quantity of the stained sediment 94 (e.g. one drop or approximately 50 μl) is placed on the microscope slide 70 (see FIG. 13) and the coverslip 72 is placed over the stained sediment 94 and over the slide 70. The quantity of stained sediment 94 is subsequently examined for parasites using the microscope 76 equipped with an ultraviolet light source (e.g. a fluorescence microscope). When the quantity of the admixture 94 is viewed through the fluorescence microscope, the following by way of example only and not by limitation may be seen; intestinal parasites 185 (e.g. *Dientamoeba fragilis*), typically having an orange to red cytoplasmic color 86 and including nuclei with a green color 87; bacteria 88 and undigested food material 89 also both typically having a green color; and a residual field or background 200, typically having a black color. As previously indicated, the biological staining agent (i.e. the acridine base compound) differentially stains the parasites such that a human eye looking through the microscope 76 can detect the parasites. As further previously indicated above, when acridine orange is employed and *Dientamoeba fragilis* is to be detected in the intestinal mucosa sample, a sharp contrast results from the *Dientamoeba fragilis* having an orange to bright red color when contrasted against a background, which is a different color from an orange to bright red color.

The invention will be illustrated by the following set forth examples which are given by way of illustration and not by any limitation. All parameters such as mixing proportions, time(s), etc. submitted in these examples are not to be construed to unduly limit the scope of the invention.

EXAMPLE I

Figure 8:
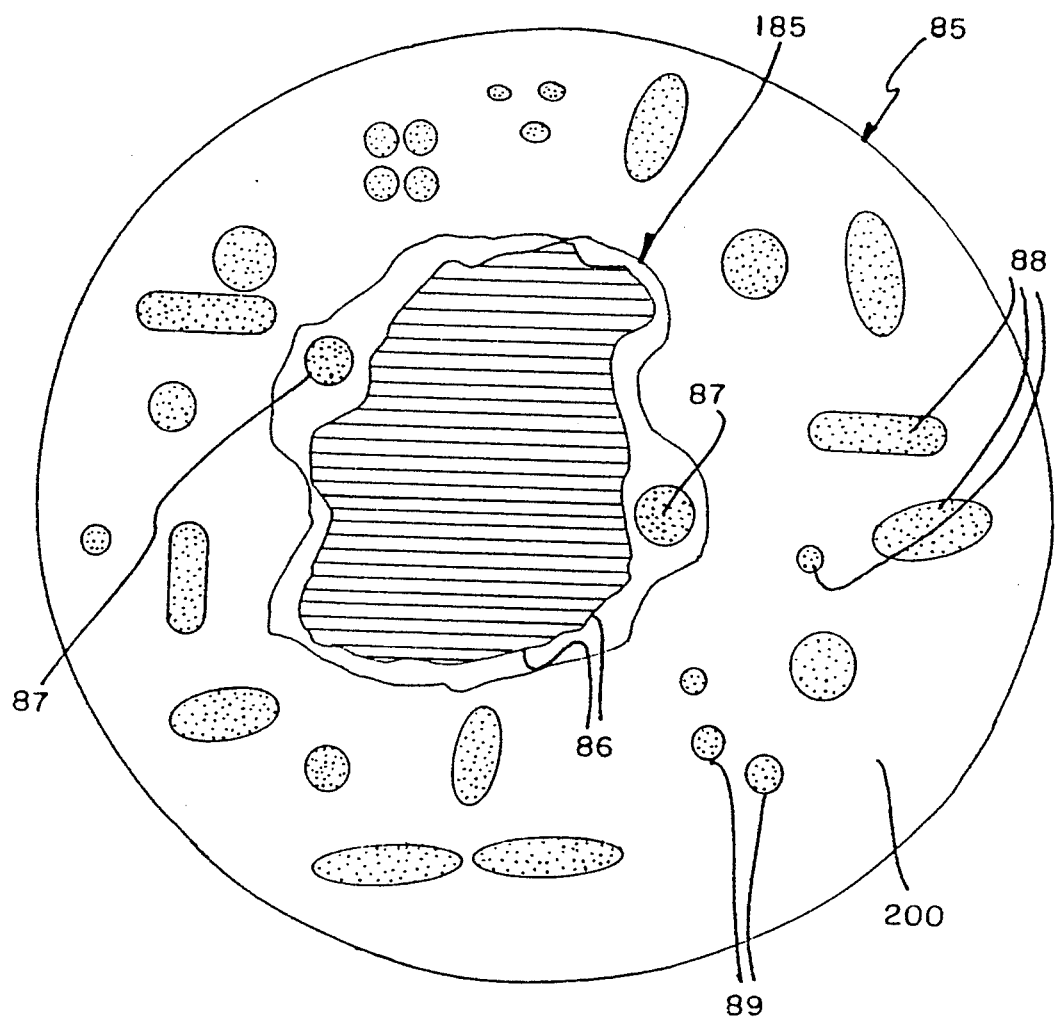
FIG. 8 is a top plan view of the differentially stained bottom sediment mixture as viewed through the fluorescence microscope of FIG. 7 at a high magnification, for viewing intestinal parasites (e.g. *Dientamoeba flagilis*) typically having an orange to red cytoplasmic color; nuclei, bacteria and undigested food material, all typically having a green color; and a residual field or background, typically having a black color.

Swab a rectal canal of a patient with sterile cotton tip 44 of one or more swabs 40 to obtain an intestinal mucosa sample; or obtain sample from feces of the patient. Immediately suspend sample in HBSS or PBS (or the aqueous solution 13 as previously described) by swirling the cotton tip 44 in the solution 13; or, in the case of feces, emulsify and suspend approximately 0.5 cubic centimeters in the solution 13. Within 24 hours in the case of the solution 13 containing no fixative and/or preservative, within four days in the case of the solution 13 being refrigerated at about 4° C. or containing a preservative such as an alcohol, and within 6 months, in the case of solution 13 containing a fixative such as formalin, centrifuge sample to produce a supernatant 50 and sediment 52 and subsequently slowly decant supernatant to obtain a sediment. Add an equal volume of 14.4 micrograms/milliliter acridine orange in HBSS or PBS (i.e. the solution 15) to the sediment to obtain a sample/stain mixture 85. Place 1 drop (approximately 50 μl) of sample/stain 85 on a microscope slide 70 and place a coverslip 72 on top of sample/stain 85 drop. Examine for parasites using microscope equipped with an ultraviolet light source (e.g. a fluorescence microscope). Parasites are detectable by being differentially stained by acridine orange as depicted in FIG. 8.

EXAMPLE II

Swab a rectal canal of a patient with sterile cotton tip 44 to obtain an intestinal mucosa sample; or obtain sample from feces of the patient. Immediately suspend sample in HBSS or PBS (or the aqueous solution 32 as previously described) with 14.4 micrograms/milliliter of acridine orange stain by swirling the cotton tip 44 in the solution 32 or, in the case of feces, emulsify and suspend approximately 0.5 cubic centimeters in the solution. Within 24 hours centrifuge sample to produce supernatant 92, and sample/stain sediment 94. Slowly decant supernatant 92 and place 1 drop (approximately 50 μl) of sample/stain sediment 94 on a microscope slide 70 and place a coverslip 72 on top of drop. Examine for parasites using microscope 76 equipped with an ultraviolet light source (e.g. a fluorescence microscope). Parasites are detectable by being differentially-stained as best shown in FIG. 14.

EXAMPLE III

Swab intestinal mucosa in a rectal canal of a patient with sterile cotton tip 44 of one or more swabs 40 to obtain an intestinal mucosa sample; or obtain sample from feces of the patient. Immediately suspend sample in HBSS or PBS (or the aqueous solution 13 as described above) by swirling the cotton tip 44 in the solution; or, in the case of feces, emulsify and suspend approximately 0.5 cubic centimeters in the solution 13. Within 24 hours in the case of the solution 13 containing no fixative and/or preservative, within four days in the case of the solution 13 being refrigerated at about 4° C. or containing a preservative such as an alcohol, and within 6 months, in the case of solution 13 containing a fixative such as formalin, centrifuge sample to produce a supernatant 50 and sediment 52 and subsequently slowly decant supernatant to obtain a sediment. Spread a thin layer of emulsified bottom sediment on a microscope slide and allow to dry. Stain emulsified dried bottom sediment by placing enough acridine orange solution (14.4 micrograms/milliliter in HBSS or the solution 15 as described above) to cover the thin layer of dried bottom sediment for 2 minutes. Then rinse side of microscope slide having dried bottom sediment covered with acridine orange solution with water and allow to dry. Place one drop (approx. 50 µl) of PBS or HBSS or suitable mounting medium on the rinsed side of the slide 70 and cover with cover slip 72. Examine for parasites using microscope equipped with an ultraviolet light source (e.g. fluorescence microscope). Parasites are detectable by being differentially stained as best shown in FIG. 8.

EXAMPLE IV

Swab intestinal mucosa in a rectal canal of a patient with sterile cotton tip 44 of one or more swabs 40 to obtain an intestinal mucosa sample; or obtain sample from feces of a patient. Immediately suspend sample in HBSS or PBS (or the aqueous solution 13 as previously described) by swirling the cotton tip 44 in the solution 13 or, in the case of feces, emulsify and suspend approximately 0.5 cubic centimeters in the solution 13. Within 24 hours in the case of the solution 13 containing no fixative and/or preservative, within four days in the case of the solution 13 being refrigerated at about 4° C. or containing a preservative such as an alcohol, and within 6 months, in the case of solution 13 containing a fixative such as formalin, centrifuge sample to produce a supernatant 50 and sediment 52 and subsequently slowly decant supernatant to obtain a sediment. Slowly decant supernatant and spread a thin layer of emulsified bottom sediment on a microscope slide and allow to dry. Fix dried bottom sediment by covering with 30% by volume ethanol/70% by volume HBSS for 2 minutes, rinse side of microscope slide having dried bottom sediment covered with ethanol/HBSS with water and air dry. Stain rinsed side of slide by placing enough acridine orange solution (14.4 micrograms/milliliter in HBSS or the solution 15 as described above) to cover the rinsed fixed layer for 2 minutes. Then, rinse side of microscope slide having the stained, fixed, dried bottom sediment with water and allow to dry. Place one drop (approx. 50 µl) of PBS or HBSS or suitable mounting medium on the rinsed side of slide and cover with cover slip 72. Examine for parasites using microscope 76 equipped with an ultraviolet light source (e.g. fluorescence microscope). Parasites are detectable by being differentially stained as best shown in FIG. 8.

EXAMPLE V

Swab intestinal mucosa in a rectal canal of a patient with sterile cotton tip 44 of one or more swabs 40 to obtain an intestinal mucosa sample; or obtain sample from feces of the patient. Immediately suspend sample in HBSS or PBS (or the aqueous solution 13 as previously described) by swirling the cotton tip 44 in the solution 13; or, in the case of feces, emulsify and suspend approximately 0.5 cubic centimeters in the solution 13. Within 24 hours in the case of the solution 13 containing no fixative and/or preservative, within four days in the case of the solution 13 being refrigerated at about 4° C. or containing a preservative such as an alcohol, and within 6 months, in the case of solution 13 containing a fixative such as formalin, centrifuge sample to produce a supernatant 50 and sediment 52 and subsequently slowly decant supernatant to obtain a sediment. Slowly decant supernatant and spread a thin layer of emulsified bottom sediment on a microscope slide and allow to dry. Fix dried bottom sediment by covering with 30% by volume ethanol/70% by volume HBSS for 2 minutes, rinse side of microscope slide having dried bottom sediment covered with ethanol/HBSS with water and air dry. Stain rinsed side of slide by placing enough acridine orange solution 15 (14.4 micrograms/milliliter in HBSS or the solution 15 as described above) to cover rinsed, fixed bottom sediment layer for 2 minutes, then rinse side of microscope slide having the stained, rinsed fixed bottom sediment with water and allow to dry. Permanently fix sediment on slide by covering the rinsed, stained bottom sediment with 10% formalin for 2 minutes, rinse side of microscope slide having the permanently fixed, stained bottom sediment with water and allow to air dry. Place one drop (approx. 50 µl) of PBS or HBSS or suitable mounting medium on the rinsed side of the slide and cover with cover slip 72. Examine for parasites using microscope 76 equipped with an ultraviolet light source (e.g. a fluorescence microscope). Parasites are detectable by being differentially stained as best shown in FIG. 8.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:
1. A method for determining if Dientamoeba fragilis is present in a fecal material from a human being comprising the steps of:
   (a) obtaining from a human being a fecal sample;
   (b) contacting the obtained fecal sample of step (a) with an acridine solution in a weight ratio ranging from about 1:10 to about 10:1 such that if Dientamoeba fragilis is present in the fecal sample, the *Dientamoeba fragilis* becomes stained with a first color, and such that if residual fecal material is present in the fecal sample, the residual fecal material becomes stained with a second color, said acridine solution comprising an aqueous solution and from about 0.40 micrograms/milliliter to about 100 micrograms/milliliter of an acridine biological staining compound; and
   (c) viewing through a fluorescence microscope the obtained fecal sample of step (b) after being contacted with the acridine solution of step (b) and detecting and discovering the presence of the first color, signifying the presence of Dientamoeba fragilis in the fecal sample, and further detecting and discovering the presence of the second color, signifying the presence of the residual fecal material in the fecal sample.

2. The method of claim 1 wherein said first color is an orange to red cytoplasmic color.

3. The method of claim 2 wherein said contacting step (b) includes contacting the obtained fecal sample with said acridine solution in said weight ratio ranging from about 1:10 to about 10:1 such that if a residual field is present in a microscopic field of view of the fecal sample, the residual field it possesses a third color5; and said viewing step (c) additionally comprises detecting and discovering the presence of the third color in a microscopic field of view of the fecal sample, signifying the presence of the residual field in the microscopic field of view of the fecal sample.

4. The method of claim 3 wherein said third color is a black color.

5. The method of claim 4 wherein said second color is a green color.

6. The method of claim 5 wherein said acridine biological staining compound is acridine orange.

7. The method of claim 2 wherein said second color is a green color.

8. The method of claim 1 wherein said second color is a green color.

9. The method of claim 8 wherein said contacting step (b) includes contacting the obtained fecal sample with said acridine solution in said weight ratio ranging from about 1:10 to about 10:1 such that if a residual field is present in a microscopic field of view of the fecal sample, the residual field becomes stained with a third color; and said viewing step (c) additionally comprises detecting and discovering the presence of the third color in a microscopic field of view of the fecal sample, signifying the presence of the residual field in the microscopic field of view of the sample.

10. The method of claim 9 wherein said third color is a black color.

11. The method of claim 1 wherein said contacting step (b) includes contacting the obtained fecal sample with said acridine solution in said weight ratio ranging from about 1:10 to about 10:1 such that if a residual field is present in a microscopic field of view of the fecal sample, the residual field possesses a third color; and said viewing step (c) additionally comprises detecting and discovering the presence of the third color in a microscopic field of view of the fecal sample, signifying the presence of the residual field in the microscopic field of view of the fecal sample.

12. The method of claim 11 wherein said third color is a black color.

13. The method of claim 1 wherein said acridine biological staining compound is acridine orange.

14. A method for determining if Dientamoeba fragilis is present in fecal material from a human being comprising the steps of:
 (a) obtaining from a human being sample of step (a) with an acridine solution in a weight ratio ranging from about 1:10 to about 10:1 such that if Dientamoeba fragilis is present in the fecal sample, the Dientamoeba fragilis becomes stained with a first color, and such that said residual material fecal becomes stained with a second color that is different from the first color, said acridine solution comprising an aqueous solution and from about 0.40 micrograms/ milliliter to about 100 micrograms/-milliliter of an acridine biological staining compound; and
 (c) viewing through a fluorescence microscope the obtained fecal sample of step (b) after being contacted with the acridine solution of step (b) and detecting and discovering the presence of the first color, signifying the presence of Dientamoeba fragilis in the fecal sample, and further detecting and discovering the presence of the second color, signifying the presence of the residual fecal material in the fecal sample.

15. A method for determining if Dientamoeba fragilis is present in fecal material from a human being comprising the steps of:
 (a) obtaining from a human being a fecal sample;
 (b) mixing the obtained fecal sample with an aqueous salt solution to obtain a mixture of fecal material and aqueous salt solution;
 (c) centrifuging the mixture of step (b) to produce a supernatant and sediment;
 (d) removing the sediment of step (c) from the supernatant;
 (e) contacting the removed sediment of step (d) with an acridine solution in a weight ratio ranging from about 1:10 to about 10:1 such that if Dientamoeba fragilis is present in the sediment, the Dientamoeba fragilis becomes stained with a first color, and such that if a residual fecal material is present in the sediment, the residual fecal material becomes stained with a second color, and such that further if a residual field is present in a microscopic field of view of the sediment, the residual field possesses a third color, said acridine solution comprising an aqueous solution and from about 0.40 micrograms/milliliter to about 100 micrograms/milliliter of an acridine biological staining compound; and
 (f) viewing through a fluorescence microscope the removed sediment of step (e) after being contacted with the acridine solution of step (e) and detecting and discovering the presence of the first color, signifying the presence of Dientamoeba fragilis in the removed sediment and in the fecal sample, and further detecting and discovering the presence of the second color, signifying the presence of the residual fecal material in the removed sediment and in the fecal sample, and yet further detecting and discovering the presence of the third color, signifying the presence of the residual field in the microscopic field of view of the sediment.

16. The method of claim 15 wherein said acridine biological staining compound is acridine orange.

17. The method of claim 16 wherein said color is an orange to red cytoplasmic color.

18. The method of claim 17 wherein said second color is a green color and said third color is a black color.

19. The method of claim 18 wherein said residual fecal material having the second color of a green color comprises bacteria, undigested food material, mycobacteria, and epithelial cells.

20. The method of claim 19 wherein said aqueous salt solution of step (b) comprises a pH indicator, from about 1% by volume to about 70% by volume 4 of a fixative, and an alcohol preservative and wherein said aqueous salt solution exhibits an osmolality ranging from about 200 milliOsm/liter to about 400 milliOsm/liter and contains one or more of the following ingredients: sodium chloride, potassium chloride, potassium phosphate, sodium phosphate and glucose.

* * * * *